(12) United States Patent (10) Patent No.: US 8,361,306 B2
Teramoto et al. (45) Date of Patent: Jan. 29, 2013

(54) GAS SENSOR CONTROL APPARATUS AND METHOD

(75) Inventors: Satoshi Teramoto, Nisshin (JP);
Hirotaka Onogi, Kakamigahara (JP);
Koji Shiotani, Kasugai (JP); Kenji Kato, Nagoya (JP); Takashi Kawai, Komaki (JP)

(73) Assignee: NGK Spark Plug Co., Ltd., Aichi (JP)

( * ) Notice: Subject to any disclaimer, the term of this patent is extended or adjusted under 35 U.S.C. 154(b) by 484 days.

(21) Appl. No.: 12/630,423

(22) Filed: Dec. 3, 2009

(65) Prior Publication Data

US 2010/0140113 A1 Jun. 10, 2010

(30) Foreign Application Priority Data

Dec. 4, 2008 (JP) .................................. 2008-309504
Oct. 15, 2009 (JP) .................................. 2009-238503

(51) Int. Cl.
*G01N 27/26* (2006.01)
*G01N 27/417* (2006.01)

(52) U.S. Cl. ...................... 205/784.5; 205/782; 205/781; 205/783.5; 73/23.31; 73/23.32; 204/424; 204/425

(58) Field of Classification Search ................... 205/782, 205/781, 783.5–785; 204/411, 421–429; 73/23.31, 23.32
See application file for complete search history.

(56) References Cited

U.S. PATENT DOCUMENTS

| 4,804,454 A | * | 2/1989 | Asakura et al. | 204/406 |
| 2003/0106808 A1 | * | 6/2003 | Miyata et al. | 205/761 |
| 2004/0238378 A1 | * | 12/2004 | Kumazawa et al. | 205/781 |

FOREIGN PATENT DOCUMENTS

| JP | 11-304758 A | 11/1999 |
| JP | 2001-141696 A | 5/2001 |
| JP | 2001-281211 | * 10/2001 |
| JP | 2001-281211 A | 10/2001 |

OTHER PUBLICATIONS

Machine translation of JP 2001-281211.*

* cited by examiner

*Primary Examiner* — Jeffrey T Barton
*Assistant Examiner* — Jennifer Dieterle
(74) *Attorney, Agent, or Firm* — Sughrue Mion, PLLC

(57) ABSTRACT

There is provided a control apparatus for a gas sensor, which has a sensor element equipped with first and second oxygen pumping cells. The sensor control apparatus is configured to drive the first oxygen pumping cell to adjust the oxygen concentration of gas under measurement, drive the second oxygen pumping cell to produce a flow of electric current according to the amount of oxygen pumped out of the oxygen concentration adjusted gas by the second oxygen pumping cell, perform specific drive control to control the amount of oxygen pumped by the second oxygen pumping cell to a predetermined level after startup of the sensor element and before the application of the drive voltage between the electrodes of the second oxygen pumping cell.

5 Claims, 7 Drawing Sheets

GAS SENSOR CONTROL APPARATUS AND METHOD

BACKGROUND OF THE INVENTION

The present invention relates to an apparatus and method for controlling a gas sensor, which is capable of detecting a specific gas component in a gas under measurement, and more particularly to control of the gas sensor at startup.

Various gas sensors are used to measure the concentration of a specific gas component e.g. nitrogen oxide (NOx) or ammonium in a gas under measurement such as an exhaust gas from an internal combustion engine. For example, there is known a NOx sensor that includes a sensor element equipped with an oxygen concentration detection cell and first and second oxygen pumping cells, each of which has an oxygen ion conducting solid electrolyte layer and a pair of porous electrodes arranged on the solid electrolyte layer, to define first and second measurement chambers. When a gas under measurement first flows into the first measurement chamber, the first oxygen pumping cell pumps oxygen in or out of the first measurement chamber so as to adjust the oxygen concentration of the gas under measurement in the first measurement chamber to a given level and thereby maintain the output voltage of the oxygen concentration detection cell at a constant value. When the gas under measurement flows from the first measurement chamber into the second measurement chamber, the second oxygen pumping cell pumps oxygen out of the second measurement chamber with the application of a constant drive voltage between the porous electrodes so as to produce a flow of electric current through the second oxygen pumping cell according to the amount of oxygen dissociated from NOx in the gas in the second measurement chamber and pumped out by the second oxygen pumping cell. The NOx concentration of the gas under measurement can be thus determined based on the current output of the second oxygen pumping cell.

In the case of using this type of NOx sensor to measure the NOx concentration in the engine exhaust gas, the second measurement chamber changes into a lean state (close to the air atmosphere) during a lapse of time from the end of the previous operation to the restart of the engine. In order to bring the second measurement chamber into a low oxygen concentration state quickly at startup of the sensor element and shorten the stabilization time required for the NOx sensor to become ready for stable NOx concentration measurement, Japanese Laid-Open Patent Publication No. 2001-281211 and No. 2001-141696 propose so-called preliminary drive control of the second oxygen pumping cell to pump oxygen out of the second measurement chamber forcefully with the application of a constant voltage higher than that in normal drive control.

SUMMARY OF THE INVENTION

It is however known that, when the applied voltage of the second oxygen pumping cell becomes higher than or equal to a given value, the dissociation of water ($H_2O$) occurs at the porous electrode of the second oxygen pumping cell, and the limit of the current of the second oxygen pumping cell increases with the $H_2O$ concentration. Namely, the amount of oxygen pumped by the second oxygen pumping cell varies with the $H_2O$ concentration when the applied voltage of the second oxygen pumping cell becomes higher than or equal to the given value. The above-proposed conventional preliminary drive control presents a problem that the stabilization time of the gas sensor changes depending on the $H_2O$ concentration due to the application of the higher voltage than that in the normal drive control. This problem arises in not only the NOx sensor but also any other types of sensors using oxygen pumping cells.

It is therefore an object of the present invention to provide an apparatus and method for controlling a gas sensor so as to ensure a uniform stabilization time of the gas sensor at sensor startup.

According to one aspect of the present invention, there is provided a control apparatus for a gas sensor, the gas sensor comprising a sensor element equipped with first and second oxygen pumping cells to define first and second measurement chambers so that a gas under measurement first flows in the first measurement chamber and then flows from the first measurement chamber into the second measurement chamber, each of the first and second oxygen pumping cells having an oxygen ion conductor and a pair of electrodes arranged on the oxygen ion conductor, the control apparatus being configured to: drive the first oxygen pumping cell in such a manner that the first oxygen pumping cell pumps oxygen in or out of the first measurement chamber to adjust the oxygen concentration of the gas in the first measurement chamber; drive the second oxygen pumping cell with the application of a drive voltage between the electrodes of the second oxygen pumping cell in such a manner that the second oxygen pumping cell pumps oxygen out of the second measurement chamber to produce a flow of electric current between the electrodes of the second oxygen pumping cell in accordance with the amount of the oxygen pumped by the second oxygen pumping cell; determine the concentration of a specific gas in the gas under measurement based on the electric current between the electrodes of the second oxygen pumping cell; and perform specific drive control to control the amount of the oxygen pumped by the second oxygen pumping cell to a predetermined level after startup of the sensor element and before the application of the drive voltage between the electrodes of the second oxygen pumping cell.

According to another aspect of the present invention, there is provided a control method for a gas sensor, the gas sensor comprising a sensor element equipped with first and second oxygen pumping cells to define first and second measurement chambers so that a gas under measurement first flows in the first measurement chamber and then flows from the first measurement chamber into the second measurement chamber, each of the first and second oxygen pumping cells having an oxygen ion conductor and a pair of electrodes arranged on the oxygen ion conductor, the control method comprising: driving the first oxygen pumping cell in such a manner that the first oxygen pumping cell pumps oxygen in or out of the first measurement chamber to adjust the oxygen concentration of the gas in the first measurement chamber; driving the second oxygen pumping cell with the application of a drive voltage between the electrodes of the second oxygen pumping cell in such a manner that the second oxygen pumping cell pumps oxygen out of the second measurement chamber to produce a flow of electric current between the electrodes of the second oxygen pumping cell in accordance with the amount of the oxygen pumped by the second oxygen pumping cell; determining the concentration of a specific gas in the gas under measurement based on the electric current between the electrodes of the second oxygen pumping cell; and performing specific drive control to control the amount of the oxygen pumped by the second oxygen pumping cell to a predetermined level after startup of the sensor element and before the application of the drive voltage between the electrodes of the second oxygen pumping cell.

The other objects and features of the present invention will also become understood from the following description.

DESCRIPTION OF THE EMBODIMENTS

Figure 1:
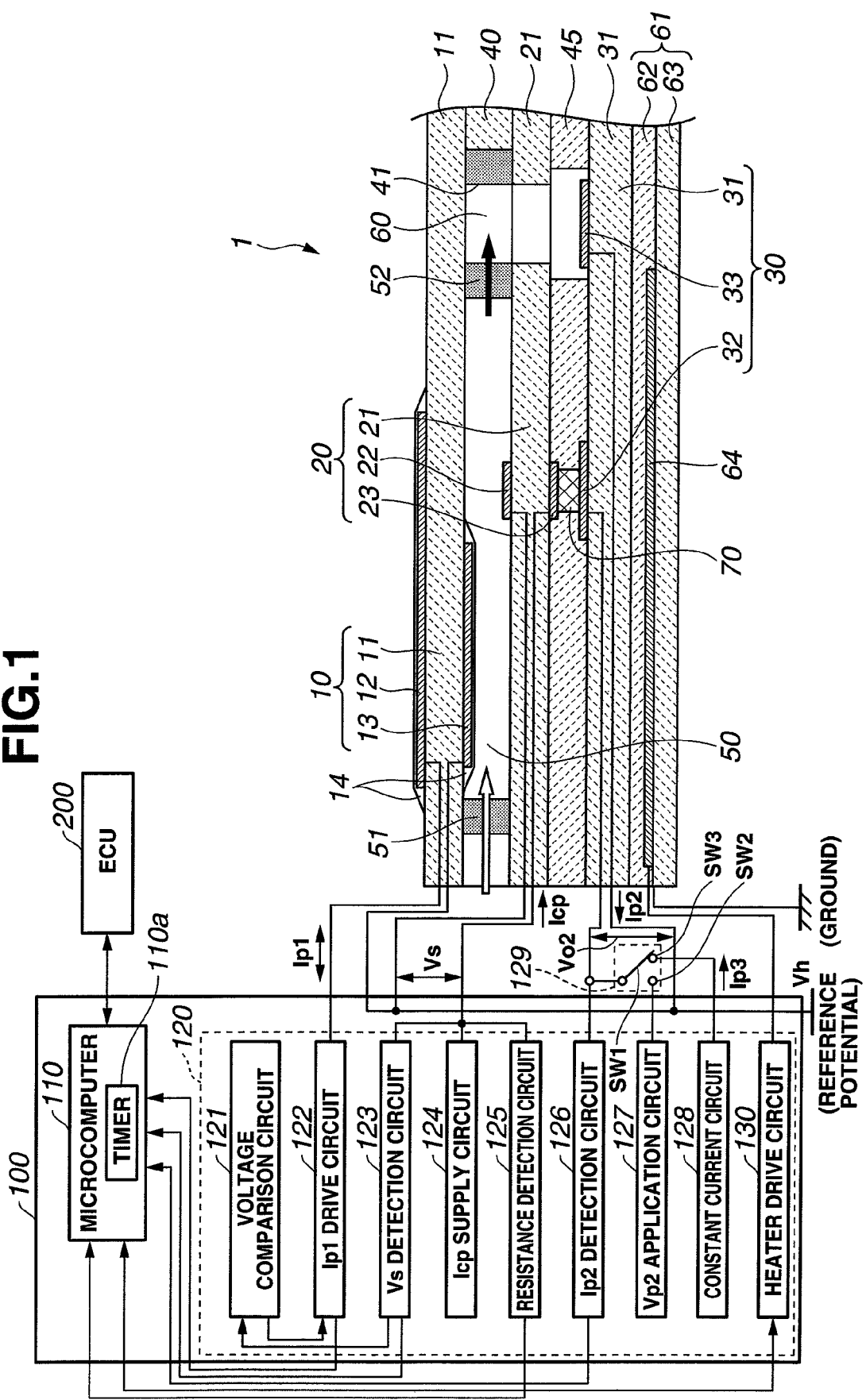
FIG. 1 is a schematic view of a gas sensor system with a gas sensor and a sensor control apparatus according to a first embodiment of the present invention.

The present invention will be described in detail below by way of the following first and second embodiments, in which like parts and portions are designated by like reference numerals to avoid repeated explanations thereof. It is herein noted that: the term "front" refers to a gas sensing side with respect to the direction of an axis of a gas sensor; and the term "rear" refers to a side opposite the front side for purposes of illustration.

First Embodiment

Referring to FIG. 1, a gas sensor system according to the first embodiment of the present invention is designed for use in an internal combustion engine and includes a gas sensor having a sensor element 1 and a heater element 61 accommodated in a housing and mounted to an exhaust pipe of the engine to detect nitrogen oxide (NOx) in an engine exhaust gas and a sensor control apparatus 100 located separately from and electrically connected to the gas sensor (sensor element 1 and heater element 61) via lead wires to control the operations of the gas sensor and to determine the concentration of NOx in the exhaust gas based on the output of the gas sensor (sensor element 1).

The sensor element 1 has a rectangular plate shape formed with oxygen ion conducting solid electrolyte layers 11, 21 and 31 (oxygen ion conductors), insulating layers 40 and 45, porous electrodes 12, 13, 22, 23, 32 and 33 and porous gas diffusion control members 51 and 52. The solid electrolyte layers 11, 21 and 31 are made of an oxygen ion conducting material such as zirconia, whereas the porous electrodes 12, 13, 22, 23, 32 and 33 are made of e.g. Pt, a Pt alloy or a cermet of Pt and ceramic.

The solid electrolyte layers 11, 21 and 31 and the insulating layers 40 and 45 are alternately laminated together. There are a first measurement chamber 50 defined between the solid electrolyte layers 11 and 21 (in the same plane as the insulating layer 40) in communication with the sensor outside and a second measurement chamber 60 defined between the solid electrolyte layers 11 and 31 in communication with the first measurement chamber 50 so that the gas under measurement (engine exhaust gas) first flows into the first measurement chamber 50 and then flows from the first measurement gas 50 into the second measurement chamber 60. The first gas diffusion control member 51 is arranged on a front side of the first measurement chamber 50 so as to serve as a partition between the sensor outside and the first measurement chamber 50 and to regulate the amount of flow of the exhaust gas into the first measurement chamber 50 per unit time. On the other hand, the second gas diffusion control member 52 is arranged in an opening 41 of the second measurement chamber 60 so as to serve as a partition between the first and second measurement gas chambers 50 and 60 and to regulate the amount of flow of the exhaust gas into the second measurement chamber 60 per unit time. There is also a reference oxygen chamber 70 defined between the solid electrolyte layers 21 and 31 at such a position that the reference oxygen chamber 70 faces the first measurement chamber 50 via the solid electrolyte layer 21. A porous insulating ceramic member is filled in the reference oxygen chamber 70.

The porous electrodes 12 and 13 are arranged on opposite sides of the solid electrolyte layer 11 with the porous electrode 12 exposed to the sensor outside and connected to the sensor control apparatus 100 and the porous electrode 13 exposed to the first measurement chamber 50 and connected to the common reference potential (e.g. 3.6 V). When an electric current Ip1 is supplied between the porous electrodes 12 and 13 from the sensor control apparatus 100, the solid electrolyte layer 11 pumps oxygen in or out of the first measurement chamber 50 from and to the sensor outside. The solid electrolyte layer 11 and the porous electrodes 12 and 13 thus function together as an Ip1 cell 10 (first oxygen pumping cell). Further, porous ceramic protection layers 14 are formed on surfaces of the porous electrodes 12 and 13 so as to prevent the porous electrodes 12 and 13 from becoming deteriorated by exposure to any poisoning gas component (reducing atmosphere) of the exhaust gas.

The porous electrodes 22 and 23 are arranged on opposite sides of the solid electrolyte layer 21 with the porous electrode 22 exposed to the first measurement chamber 50 and connected to the common reference potential (e.g. 3.6 V) and the porous electrode 23 exposed to the reference oxygen chamber 70 and connected to the sensor control apparatus 100. There arises a voltage Vs as an electromotive force between the porous electrodes 22 and 23 in accordance with a difference in oxygen partial pressure between the first measurement chamber 50 and the reference oxygen chamber 70. The solid electrolyte layer 21 and the porous electrodes 22 and 23 thus function together as a Vs cell 20 (oxygen concentration detection cell).

The porous electrodes 32 and 33 are arranged on an inner side of the solid electrolyte layer 31 facing the solid electrolyte layer 21 with the porous electrode 33 exposed to the second measurement chamber 60 and connected to the common reference potential (e.g. 3.6 V) and the porous electrode 32 exposed to the reference oxygen chamber 70 and connected to the sensor control apparatus 100. When a constant drive voltage Vp2 is placed between the porous electrodes 32 and 33 by the sensor control apparatus 100, the solid electrolyte layer 31 pumps oxygen out of the second measurement chamber 60 into the reference oxygen chamber 70. The solid electrolyte layer 31 and the porous electrodes 32 and 33 thus function together as an Ip2 cell (second oxygen pumping cell).

The heater element 61 is arranged on an outer side of the solid electrolyte layer 31 opposite from the solid electrolyte layer 21 and has a pair of insulating sheets 62 and 63 formed predominantly of alumina and a heater pattern 42 formed predominantly of Pt and embedded between the insulating sheets 62 and 63 to generate and apply heat to the sensor element 1 by energization of the heater pattern 64.

In the case of using the above-structured gas sensor to measure the NOx concentration in the engine exhaust gas, a lean gas (close to the atmospheric air) flows and exists in the second measurement chamber 60 during a lapse of time from the end of the previous operation to the restart of the engine. In other words, a larger amount of oxygen exists in the second measurement chamber 60 before startup than during normal operation of the gas sensor. In such a lean condition, if the sensor control apparatus 100 initiates normal drive control of the Ip2 cell 30 immediately after the startup of the sensor element 1, it takes a long time (e.g. about 10 minutes) to bring the second measurement chamber 60 into such a low oxygen concentration state that the sensor element 1 becomes ready for stable NOx concentration measurement.

In order to shorten the stabilization time of the gas sensor (the time required for the sensor element 1 to become ready for stable NOx concentration measurement after the startup of the sensor element 1), the sensor control apparatus 100 is configured to perform specific preliminary drive control of the Ip2 cell 30 after the startup of the sensor element 1 so as to eject excessive oxygen from the second measurement chamber 60 forcefully in a short time by the oxygen pumping action of the Ip2 cell 30 and, after the sensor element 1 enters the stable/ready state, perform normal drive control of the Ip2 cell 30 for NOx concentration measurement. In the first embodiment, the preliminary drive control of the Ip2 cell 30 is carried out by supplying a constant electric current Ip3 between the porous electrodes 32 and 33 of the Ip2 cell 300 for a predetermined time period to control the amount of oxygen pumped by the Ip2 cell 30 per unit time to a predetermined level.

More specifically, the sensor control apparatus 100 has a microcomputer 110 and an electric circuit module 120.

The microcomputer 110 has a CPU, a RAM, a ROM, an A/D converter and an I/O interface and communicates with an engine control unit (ECU) 200 and with the electric circuit module 120 through the A/D converter and the I/O interface. The microcomputer 110 also has a timer/clock 110a set to timeout after the predetermined time period (e.g. 20 seconds).

The electric circuit module 120 has a voltage comparison circuit 121, an Ip1 drive circuit 122, a Vs detection circuit 123, an Icp supply circuit 124, a resistance detection circuit 125, a Ip2 detection circuit 126, a Vp2 application circuit 127, a constant current circuit 128 and a heater drive circuit 130 and operates under the control of the microcomputer 110.

The Icp supply circuit 124 supplies the electric current Icp between the porous electrodes 22 and 23 of the Vs cell 20. By the passage of the electric current Icp through the Vs cell 20, the Vs cell 20 is driven to pump oxygen from the first measurement chamber 50 into the reference oxygen chamber 70 and create a reference oxygen concentration atmosphere in the reference oxygen chamber 70.

The Vs detection circuit 123 detects the voltage Vs developed between the porous electrodes 22 and 23 of the Vs cell 20. The detected voltage Vs is outputted to the voltage comparison circuit 121 and to the microcomputer 110.

The voltage comparison circuit 121 compares the detected voltage Vs with a reference voltage value (e.g. 425 mV). The comparison result is outputted to the Ip1 drive circuit 122.

The Ip1 drive circuit 122 supplies the electric current Ip1 between the porous electrodes 12 and 13 of the Ip1 cell 10 while adjusting the amount and direction of flow of the electric current Ip1 according to the comparison result of the voltage comparison circuit 121 in such a manner that the electromotive voltage Vs substantially agrees with the reference voltage value. By the passage of the electric current Ip1 through the Ip1 cell 10, the Ip1 cell 10 is driven to pump oxygen in or out of the exhaust gas in the first measurement chamber 50, adjust the oxygen concentration of the exhaust gas in the first measurement chamber 50 to a given level and thereby maintain the voltage Vs between the porous electrodes 22 and 23 of the Vs cell 20 constant at the reference voltage value.

The resistance detection circuit 125 periodically supplies a given electric current to the Vs cell 20 and detects an amount of change in the voltage Vs (referred to as "voltage change amount $\Delta Vs$") caused by the passage of the given electric current through the Vs cell 20. The detected voltage change amount $\Delta Vs$ is outputted to the microcomputer 110. The microcomputer 110 stores a table showing a relationship between the voltage change amount $\Delta Vs$ and the internal resistance Rpvs of the Vs cell 20 and retrieves the internal resistance Rpvs of the Vs cell 20 from the table with reference to the detected voltage change amount $\Delta Vs$. As the internal resistance Rpvs of the Vs cell 20 is correlated with the overall temperature of the sensor element 1, the microcomputer 110 retrieves the internal resistance Rpvs of the Vs cell 20 from the table by the detected voltage change amount $\Delta Vs$ and determines the temperature of the sensor element 1 based on the internal resistance Rpvs of the Vs cell 20. The microcomputer 110 and the resistance detection circuit 125 thus constitute a temperature information reading means to read information (the internal resistance Rpvs of the Vs cell 20) correlated with the temperature of the sensor element 1. Herein, the circuit configuration of the resistance detection circuit 125 is not particularly restricted. The resistance detection circuit 125 can have any known circuit configuration as disclosed in Japanese Laid-Open Patent Publication No. 11-304758.

The Vp2 application circuit 127 applies the constant drive voltage Vp2 (e.g. 450 mV) between the porous electrodes 32 and 33 of the Ip2 cell 30 for the normal drive control of the Ip2 cell 30. When the oxygen concentration adjusted exhaust gas flows from the first measurement chamber 50 into the second measurement chamber 60 and comes into contact with the porous electrode 33 during the application of the drive voltage Vp2 between the porous electrodes 32 and 33, NOx in the gas dissociates (ionizes) into oxygen and nitrogen. The Ip2 cell 30 is driven by the application of the drive voltage Vp2 to pump oxygen out of the exhaust gas and produce a flow of electric current Ip2 between the porous electrodes 32 and 33 in accordance with the amount of oxygen ionized from NOx and pumped out of the exhaust gas in the second measurement chamber 60 by the Ip2 cell 30.

The Ip2 detection circuit 126 detects the electric current Ip2 developed between the porous electrodes 32 and 33. The detected electric current Ip2 is converted into a voltage signal and outputted to the microcomputer 110 through a differential amplifier so that the microcomputer 110 determines the NOx concentration of the exhaust gas based on the voltage signal.

The constant current circuit 128 supplies the constant electric current Ip3 (e.g. 10 µA) between the porous electrodes 32 and 33 of the Ip2 cell 30 for the preliminary drive control of the Ip2 cell 30.

The switching circuit 129 connects the porous electrode 32 of the Ip2 cell 30 to either the Vp2 application circuit 127 or the constant current circuit 128 and thereby switches between the preliminary drive control and the normal drive control. In the first embodiment, the switching circuit 129 has a first switching terminal SW1 connected with the porous electrode 32, a second switching terminal SW2 connected with the Vp2 application circuit 127 and a third switching terminal SW3 connected with the constant current circuit 128. In the normal drive control, the first and second switching terminals SW1 and SW2 are connected to each other to establish a connect between the Vp2 application circuit 127 and the porous electrode 32. In the preliminary drive control, the first and third switching terminals SW1 and SW3 are connected to each other to establish a connection between the constant current circuit 128 and the porous electrode 32.

The heater drive circuit 130 energizes the heater element 61 (heater pattern 64) by a power source to heat the sensor element 1 (Ip1 cell 10, Vs cell 20 and Ip2 cell 30) and maintain the temperature of the sensor element 1 at a given level. In the first embodiment, the heater pattern 64 is formed by a single piece of wire with one end thereof connected to the ground and the other end connected to the heater drive circuit 130; and the heater drive circuit 130 is configured to conduct PWM energization control of the heater pattern 64 under the control of the microcomputer 110 in such a manner as to adjust the internal resistance Rpvs of the Vs cell 20 and, by extension, the temperature of the sensor element 1 (Vs cell 20) to a target value.

Figure 2:
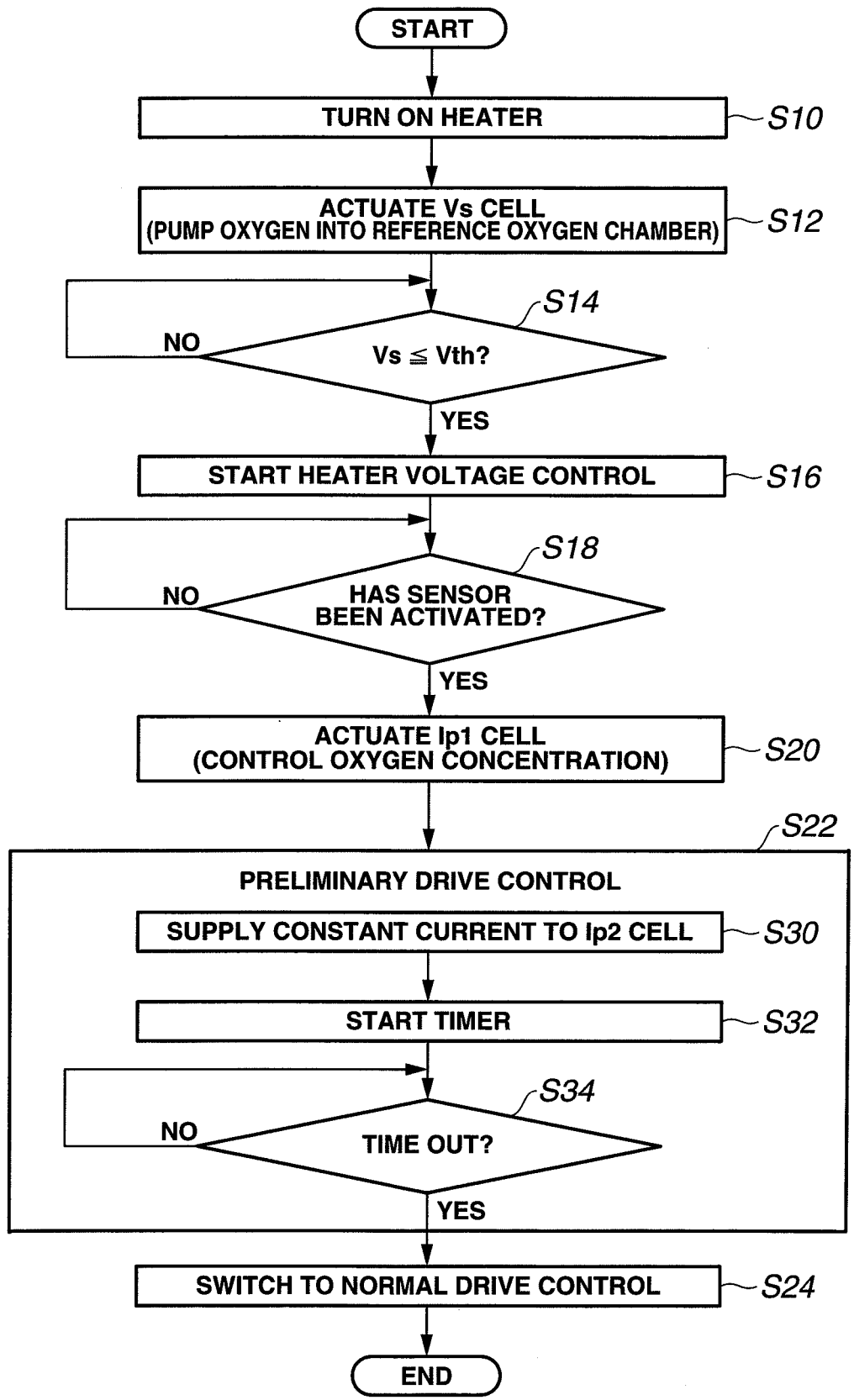
FIG. 2 is a flowchart of a sensor startup control process of the sensor control apparatus according to the first embodiment of the present invention.

As shown in FIG. 2, the microcomputer 100 executes a sensor startup control process upon receipt of a command signal from the ECU 200 at the restart of the internal combustion engine.

At step S10, the microcomputer 110 starts up the sensor element 1 and causes the heater drive circuit 130 to apply a constant voltage (e.g. 12 V) to the heater element 61 so that the heater element 61 (heater pattern 64) generates heat to activate the sensor element 1.

At step S12, the microcomputer 110 causes the Icp supply circuit 124 to supply the electric current Icp to the Vs cell 20 so that the Vs cell 20 performs its oxygen pumping action to create the reference oxygen concentration atmosphere in the reference oxygen chamber 70. In the meantime, the voltage Vs between the porous electrodes 22 and 23 gradually decreases with the internal resistance Rpvs of the Vs cell 20 as the sensor element 1 gets heated by the heater element 61.

At step S14, the microcomputer 110 reads the voltage Vs between the porous electrodes 22 and 23 from the Vs detection circuit 123 and compares the read voltage Vs with a given value Vth to check whether the voltage Vs is lower than or equal to the given value Vth. When Vs≦Vth (Yes at step S14), the control goes to step S16.

At step S16, the microcomputer 110 initiates heater voltage control (PWM energization control) to adjust the internal resistance Rpvs of the Vs cell 20 to the target value by the control of the voltage Vh applied by the heater drive circuit 130 to the heater element 61. The target value of the internal resistance Rpvs is set to e.g. 200Ω at which the temperature of the Vs cell 20 is assumed to be about 750° C.

At step S18, the microcomputer 110 reads the voltage change amount ΔVs of the Vs cell 20 from the resistance detection circuit 125, determines the internal resistance Rpvs of the Vs cell 20 with reference to the voltage change amount ΔVs and checks whether the sensor element 1 has been activated based on the internal resistance Rpvs. In the first embodiment, the microcomputer 110 checks whether the internal resistance Rpvs of the Vs cell 20 becomes lower than or equal to a threshold value, which is slightly higher than the target internal resistance value, and judges that the sensor element 1 has been properly activated (or equivalently, the temperature of the sensor element 1 becomes higher than or equal to the reference value) when the internal resistance Rpvs becomes lower than or equal to the threshold value. The threshold value of the internal resistance Rpvs is set to e.g. 300Ω at which the temperature of the Vs cell 20 is assumed to be about 650° C. Herein, the temperature of the Vs cell 20 at the time the internal resistance Rpvs reaches the threshold value is referred to as "reference temperature". As explained above, the internal resistance Rpvs of the Vs cell 20 is determined by periodically detecting and reading the voltage change amount ΔVs by the passage of the given electric current between the porous electrodes 22 and 23 of the Vs cell 20 and referring the internal resistance Rpvs of the Vs cell 20 to the table by the voltage change amount ΔVs. The control goes to step S20 when the sensor element 1 is judged as being activated properly (Yes at step S18).

At step 20, the microcomputer 110 initiates drive control of the Ip1 cell 10 so that the Ip1 cell 10 performs its oxygen pumping action to adjust the oxygen concentration of the gas in the first measurement chamber 50 by the control of the electric current Ip1 supplied from the Ip1 drive circuit 120 to the Ip1 cell 10.

At step S22, the microcomputer 110 initiates preliminary drive control of the Ip2 cell 30.

At step S30, the microcomputer 110 connects the switching terminals SW1 and SW3 of the switching circuit 129 and causes the constant current circuit 128 to supply the constant electric current Ip3 to the Ip2 cell 30.

At step 32, the microcomputer 110 starts the timer 110a.

When the constant current Ip2 is supplied to the Ip2 cell 30 for the predetermined time period in the preliminary drive control, the Ip2 cell 30 performs its oxygen pumping action to pump out oxygen to decrease the oxygen concentration of the gas in the second measurement chamber 60 to a substantially same predetermined low level at which the sensor element 1 becomes ready for NOx concentration measurement.

At step 34, the microcomputer 110 checks whether the timer 110a has timed out. When the timer 110a has timed out (Yes at step S34), the microcomputer 110 judges that the sensor element 1 has entered the stable/ready state and terminates the preliminary drive control of the Ip2 cell 30. The control then goes to step S24 to switch from the preliminary drive control to the normal drive control of the Ip2 cell 30. When the timer 110a has not timed out (No at step S34), the microcomputer 110 continues monitoring of the timer 110a.

At step S24, the microcomputer 110 connects the switching terminals SW1 and SW2 of the switching circuit 129 and causes the Vp2 application circuit 127 to apply the drive voltage Vp2 to the Ip2 cell so that the Ip2 cell 30 performs its oxygen pumping action to produce the electric current Ip2 according to the amount of oxygen dissociated from NOx and pumped out of the gas in the second measurement chamber 60 by the Ip2 cell 30. Then, the microcomputer 110 determines the NOx concentration of the exhaust gas based on the current output Ip2 of the sensor element 1 and outputs the determination result to the ECU 200 for air-fuel ratio feedback control etc.

In this way, the sensor control apparatus 100 performs specific preliminary drive control of the Ip2 cell 30 by supplying the constant current Ip3 (10 μA) to the Ip2 cell 30 for the predetermined time period (20 seconds) after the startup of the sensor element 1 and before the normal drive control of the Ip2 cell 30. The constant current Ip3 and time period of the preliminary drive control are set appropriately by experiment depending on the various conditions such as the configuration, mounting position and environment of the sensor element 1.

The effects of the preliminary drive control of the Ip2 cell 30 can be verified by the following experimental results.

Figure 3:
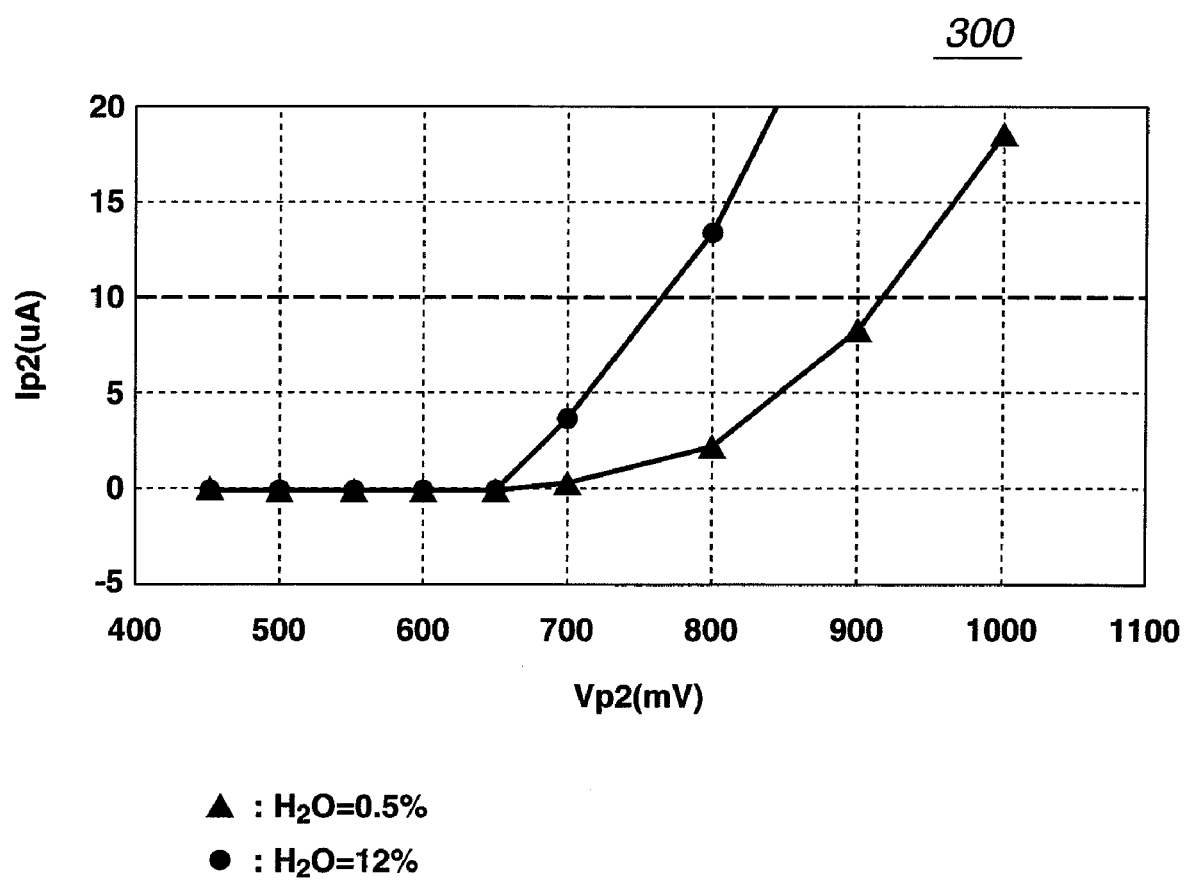
FIG. 3 is a graph showing one example of the current-voltage characteristics of an oxygen pumping cell of the gas sensor according to the first embodiment of the present invention.

An example of the current-voltage characteristics of the Ip2 cell 30 is shown in graph 300 of FIG. 3. In graph 300, the horizontal axis represents the voltage Vp2 (unit: mV) applied to the Ip2 cell 30; the vertical axis represents the current Ip2 (unit: μA) flowing through the Ip2 cell under the application of the voltage Vp2; the triangle plots represent the current-voltage characteristics of the Ip2 cell 30 in the case that the $H_2O$ concentration of the gas in the second measurement chamber 60 is 0.5%; and the circle plots represent the current-voltage characteristics of the Ip2 cell 30 in the case that the $H_2O$ concentration of the gas in the second measurement chamber 60 is 12%.

It is known that, when the applied voltage Vp2 of the Ip2 cell 30 becomes higher than or equal to a given value, the dissociation of $H_2O$ occurs at the porous electrode 33 of the Ip2 cell 30, and then, the limit of the current Ip2 (hereinafter referred to as "limit current") of the Ip2 cell 30 increases with the $H_2O$ concentration. In the first embodiment, as seen in graph 300, the dissociation of $H_2O$ occurs at the porous electrode 33 of the Ip2 cell 30 when the applied voltage Vp2 becomes higher than or equal to about 650 mV. For example, when the applied voltage Vp2 is 800 mV, the limit current of the Ip2 cell 30 is about 2.5 μA in the atmosphere where the oxygen concentration is 0.5% and is about 14 μA in the atmosphere where the oxygen concentration is 12%. In view of the fact that the amount of oxygen pumped out of the second measurement chamber 60 by the Ip2 cell 30 is proportional to the value of electric current through the Ip2 cell 30, it is evident that the ability of the Ip2 cell 30 to pump oxygen out (hereinafter referred to as "oxygen pumping ability") increases with the $H_2O$ concentration in the gas in the second measurement chamber 60 at the same applied voltage.

Figure 4:
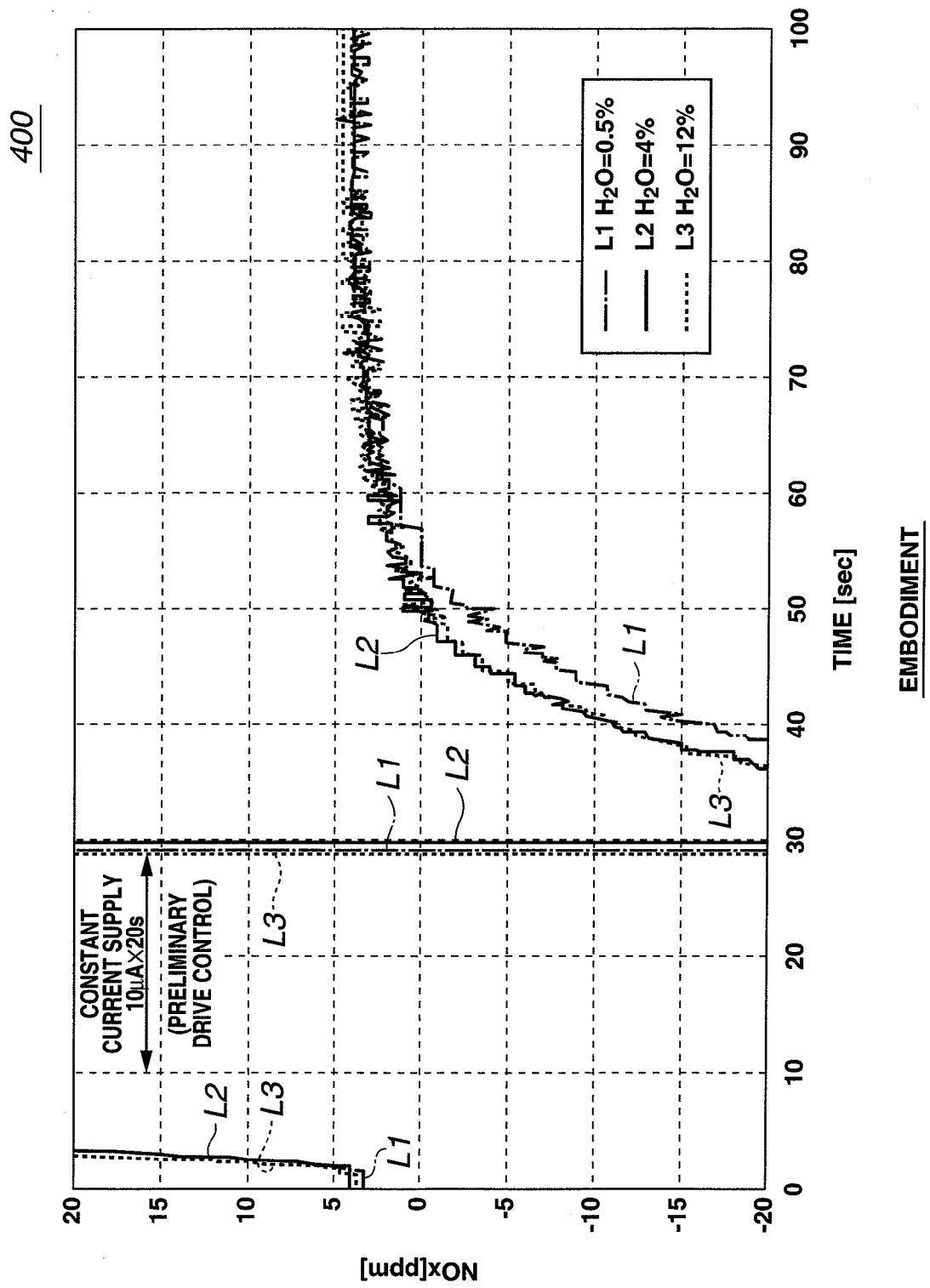
FIG. 4 is a graph showing the output of the gas sensor during the sensor startup control process according to the first embodiment of the present invention.
Figure 5:
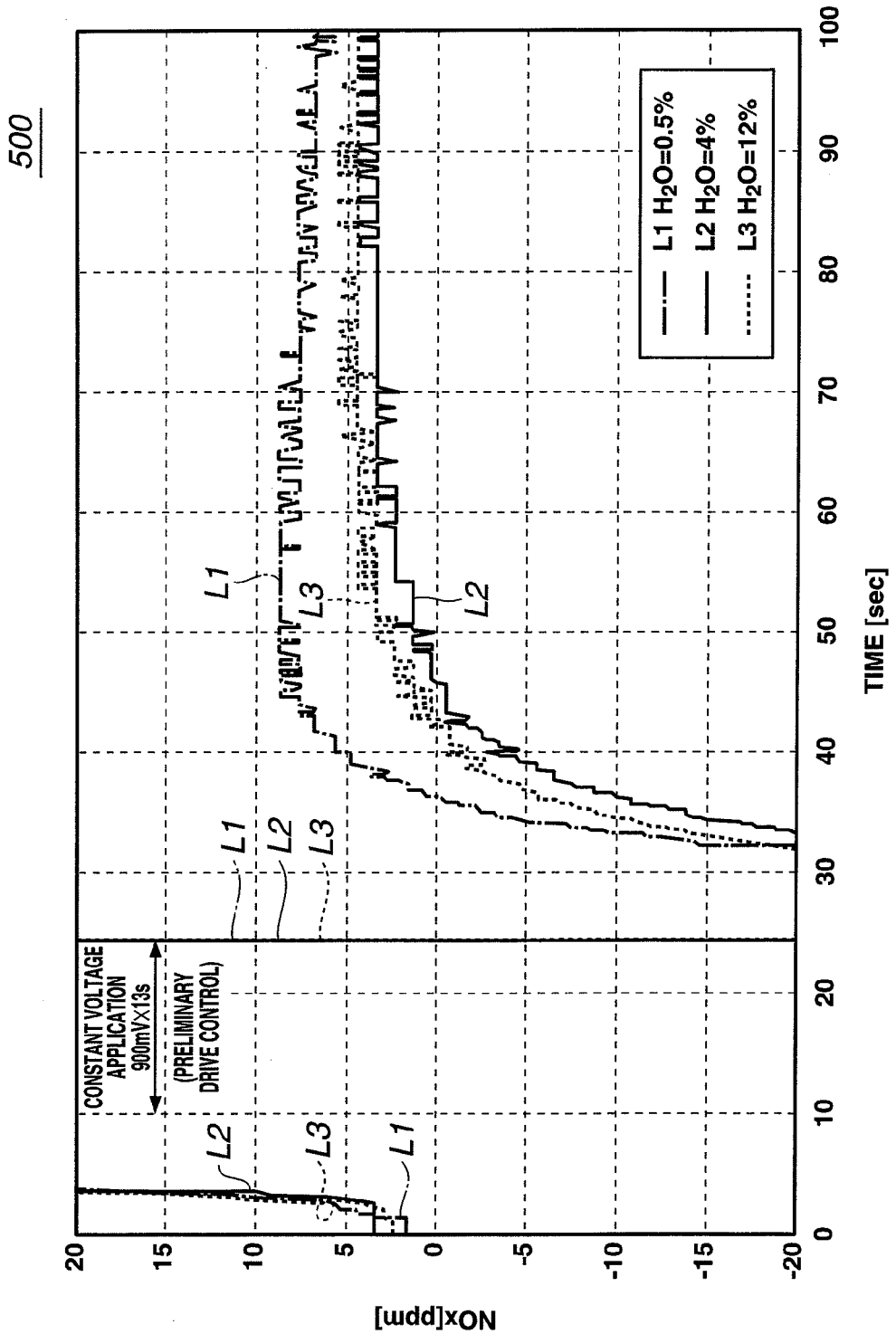
FIG. 5 is a graph showing the output of the gas sensor during a conventional sensor startup control process.

The outputs of the gas sensor during the sensor startup control process of the first embodiment and during the conventional sensor startup control process are shown in graph 400 of FIG. 4 and graph 500 of FIG. 5. In graphs 400 and 500, the horizontal axis represents the time (unit: second) lapsed after the startup of the sensor element 1; the vertical axis represents the NOx concentration (unit: ppm); the curve L1 (one-dot chain line) represents the sensor output in the case that the $H_2O$ concentration of the gas in the second measurement chamber 60 is 0.5%; the curve L2 (solid line) represents the NOx concentration measurement result in the case that the $H_2O$ concentration of the gas in the second measurement chamber 60 is 4%; and the curve L3 (dashed line) represents the sensor output in the case that the $H_2O$ concentration of the gas in the second measurement chamber 60 is 12%.

In the first embodiment, the sensor element 1 is activated during about 10 seconds from the startup of the sensor element 1 and the start of the energization of the heater element 61. After that, the preliminary drive control is initiated. As explained above, the constant electric current Ip3 (10 μA) is supplied to the Ip2 cell 30 for the predetermine time period (20 seconds) under the preliminary drive control in the first embodiment. The Ip2 cell 30 pumps excessive oxygen out of the second measurement chamber 60 forcefully so as to decrease the oxygen concentration in the second measurement chamber 60 to the predetermined low level during the preliminary drive control. When the normal drive control is conducted after completion of the preliminary drive control, the Ip2 cell 30 pumps oxygen back from the reference oxygen chamber 70 into the second measurement chamber 60 so as to increase to the oxygen concentration in the second measurement chamber 60 to the reference level corresponding to the drive voltage Vp2 (450 mV). As a result, the sensor output rises from the negative side immediately after switching from the preliminary drive control to the normal drive control as seen in graph 400.

As the amount of oxygen pumped out of the second measurement chamber 60 by the Ip2 cell 30 is proportional to the value of electric current through the Ip2 cell 30 as explained above, the Ip2 cell 30 pumps substantially the same predetermined amount of oxygen out of the second measurement chamber 60 by the supply of the constant electric current Ip3 during the preliminary drive control. The oxygen concentration in the gas in the second measurement chamber 60 thus reaches substantially the same low level (rich atmosphere) at the completion of the preliminary drive control regardless of the $H_2O$ concentration in the second measurement chamber 60. There is almost no difference in the manner in which the oxygen is pumped back from the reference oxygen chamber 70 into the second measurement chamber 60 after the preliminary drive control in the first embodiment. As shown in graph 400, the gradients of the sensor output curves L1, L2 and L3 after the preliminary drive control substantially agree with one another without depending on the $H_2O$ concentration. The sensor element 1 becomes stable at about 50 to 60 seconds after the startup of the sensor element 1 in either case that the $H_2O$ concentration is 0.5%, 4% or 12%. It is therefore possible to ensure the substantially uniform stabilization time of the sensor element 1, regardless of the $H_2O$ concentration in the gas under measurement, by the preliminary drive control of the first embodiment. There is no need to consider a variation in the $H_2O$ concentration in the gas under measurement in the setting of the stabilization time of the gas sensor.

Further, the preliminary drive control is initiated after the temperature of the sensor element 1 becomes higher than or equal to the reference temperature (more specifically, the internal resistance Rpvs of the Vs cell 20 becomes lower than or equal to the threshold value) in the first embodiment. Namely, the sensor element 1 has been properly activated before the initiation of the preliminary drive control. It is thus possible to make full use of the oxygen pumping ability of the Ip2 cell 30 during the preliminary drive control and shorten the stabilization time of the sensor element 1 effectively and efficiently. There is no fear that the sensor element 1 (Ip2 cell 30) will be damaged due to the resistance to the flow of the constant current Ip3 through the Ip2 cell 30 as the internal resistance of the solid electrolyte layer 31 has been lowered sufficiently before the preliminary drive control.

In the conventional sensor startup control process, by contrast, a relatively high constant voltage (e.g. 900 mV) is applied to the Ip2 cell 30 for a predetermined time period (e.g. 13 seconds) so that the Ip2 cell 30 pumps oxygen out of the second measurement chamber 60 during the preliminary drive control. As the limit current of the Ip2 cell 30 increases with the $H_2O$ concentration under high applied voltage conditions as explained above, the oxygen pumping ability of the Ip2 cell 30 during such high constant voltage drive control increases with the $H_2O$ concentration. The oxygen concentration in the gas in the second measurement chamber 60 at the completion of the preliminary drive control decreases with increase in the $H_2O$ concentration in the conventional sensor startup control process. Thus, the manner in which the oxygen is pumped back from the reference oxygen chamber 70 into the second measurement chamber 60 after the preliminary drive control varies depending on the $H_2O$ concentration. As shown in graph 500, the sensor output curve L1 in the atmosphere where the $H_2O$ concentration is 0.5% (close to the stoichiometric atmosphere) rises up earlier and more sharply than the sensor output curve L2, L3 in the atmosphere where the $H_2O$ concentration is 4% or 12%. The sensor output curves L1, L2 and L3 after the preliminary drive control do not agree with one another until about 100 seconds has elapsed from the startup of the sensor element 1. The stabilization time of the gas sensor (sensor element 1) is about 100 seconds in the atmosphere where the $H_2O$ concentration is 0.5% and is about 60 seconds in the atmosphere where the $H_2O$ concentration is 4% or 12%. The stabilization time of the gas sensor (sensor element 1) cannot be kept uniform regardless of the $H_2O$ concentration in the conventional sensor startup control process.

Second Embodiment

A gas sensor system with a gas sensor and a sensor control apparatus according to the second embodiment of the present invention is structurally similar to that of the first embodiment, except for the configurations of the Vp2 application circuit 127 and the switching circuit 129 and the processing operations of the microcomputer 110.

With the supply of the constant current Ip3 from the constant current circuit 128 to the Ip2 cell 30 during the preliminary drive control, the voltage (electromotive force) between the porous electrodes 32 and 33 increases as the oxygen concentration in the second measurement chamber 60 becomes decreased by the oxygen pumping action of the Ip2 cell 30. If the supply of the constant current Ip3 to the Ip2 cell 30 is continued in such a condition, there is a fear of blackening of the solid electrolyte layer 31 and, by extension, breakage of the Ip2 cell 30 due to overvoltage between the porous electrodes 32 and 33 during the preliminary drive control.

In the second embodiment, the Vp2 application circuit 127 is thus configured to not only apply the drive voltage Vp2 (e.g. 450 mV) between the porous electrodes 32 and 33 during the normal drive control, but also set the upper limit on the voltage between the porous electrodes 32 and 33 in order to prevent avoid overvoltage between the porous electrodes 32 and 33, which can cause blackening of the solid electrolyte layer 31 and breakage of the Ip2 cell 30, during the preliminary drive control.

Figure 6:
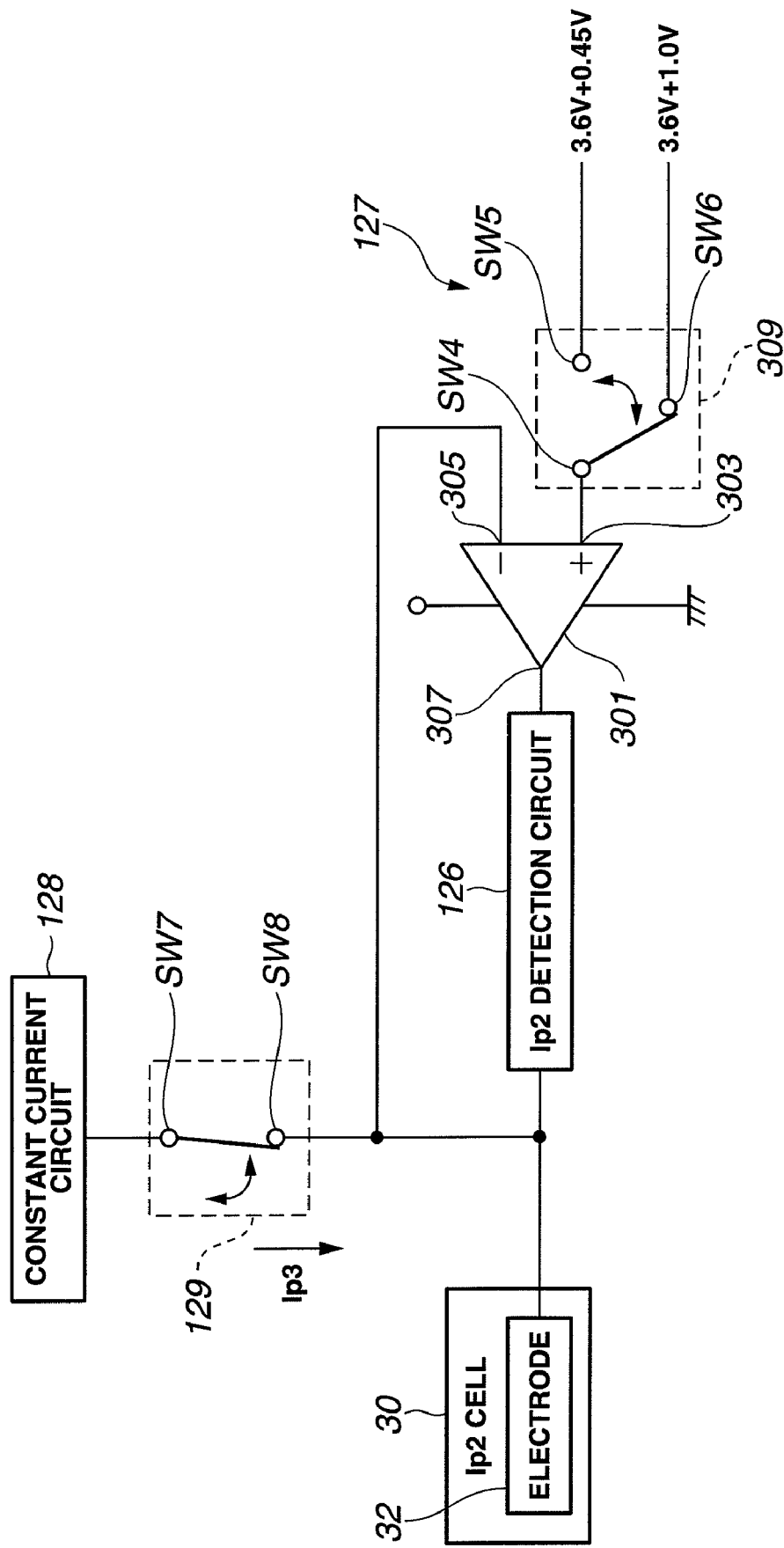
FIG. 6 is a circuit diagram of a drive voltage application circuit of a sensor control apparatus according to a second embodiment of the present invention.

As shown in FIG. 6, the Vp2 application circuit 127 has an operational amplifier 301 and a switching circuit 309 in the second embodiment. The operational amplifier 301 is driven by a constant voltage (e.g. 5 V). An output terminal 307 of the operational amplifier 301 is connected to the porous electrode 32 of the Ip2 cell 30 via the Ip2 detection circuit 126, whereas the porous electrode 33 of the Ip2 cell 30 is connected to the reference potential (e.g. 3.6 V) as in the case of the first embodiment. Herein, the Ip2 detection circuit 126 is formed with a detection resistor of a few hundred kilohms. A noninverting input terminal (+input terminal) 303 of the operational amplifier 301 is connected to either of first and second input voltages via the switching circuit 309. The first input voltage is set to a sum of the drive voltage Vp2 (e.g. 450 mV) and the reference potential (3.6 V); and the second input voltage is set to a sum of a given voltage Vli (e.g. 1.0 V) and the reference potential (3.6 V) so that the second input value is higher than the first input voltage. Further, an inverting input terminal (−input terminal) 305 of the operational amplifier 301 is electrically connected to the output terminal 307, and more specifically, to the junction point between the porous electrode 32 and one end of the resistor of the Ip2 detection circuit 126 and between the porous electrode 32 and the switching circuit 129. The switching circuit 309 has a switching terminal SW4 connected with the noninverting input terminal 303 of the operational amplifier 301, a switching terminal SW5 connected with the first input voltage and a switching circuit SW6 connected with the second input voltage so as to switch the connection of the noninverting input terminal 303 of the operational amplifier 301 to either one of the first and second input voltages.

The switching circuit 129 has a switching terminal SW7 connected with the constant current circuit 128 and a switching terminal SW8 connected with the porous electrode 32 so as to connect and disconnect the supply of the constant electric current Ip3 from the constant current circuit 128 to the Ip2 cell 30.

In the preliminary drive control, the switching terminals SW4 and SW5 are connected to each other to input the second input voltage to the noninverting input terminal 303 of the operational amplifier 301. The operational amplifier 301 outputs an electric current from the output terminal 307 so as to increase the potential of the inverting input terminal 305 until the voltage between the porous electrodes 32 and 33 of the Ip2 cell 30 exceeds the given voltage value Vli. When the voltage between the porous electrodes 32 and 33 of the Ip2 cell 30 exceeds the given voltage value Vli, the operational amplifier 301 absorbs an electric current from the constant current voltage 128 so as to decrease the potential of the inverting input terminal 305 and thereby limit the voltage between the voltage between the porous electrodes 32 and 33 of the Ip2 cell 30 to be lower than the limit voltage value Vli. On the other hand, the switching terminals SW4 and SW5 are connected to each other to input the first input voltage to the noninverting input terminal 303 of the operational amplifier 301 so that the operational amplifier 301 generates and outputs the drive voltage Vp2 to the Ip2 cell 30 in the normal drive control.

Figure 7:
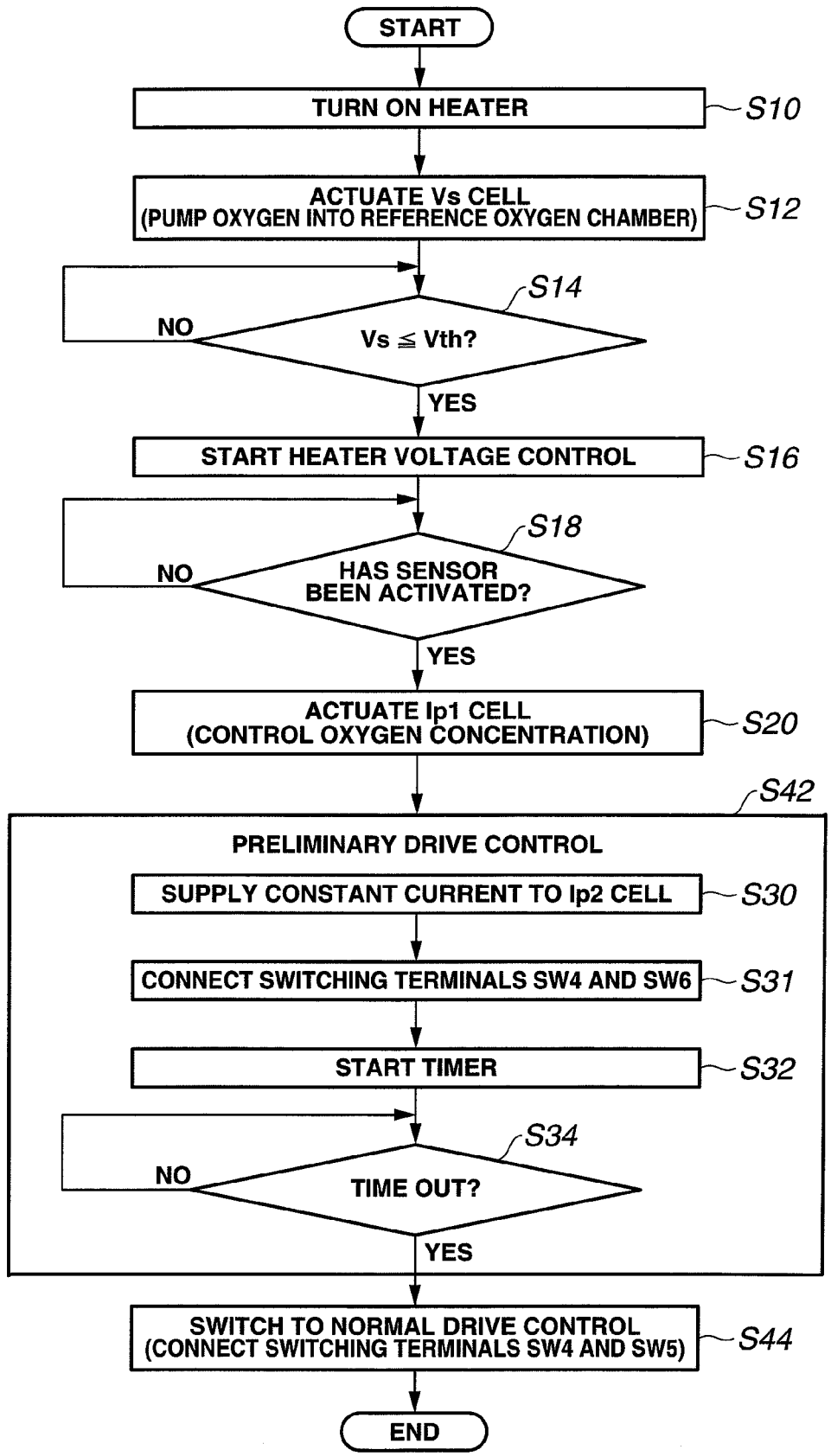
FIG. 7 is a flowchart of a sensor startup control process of the sensor control apparatus according to the second embodiment of the present invention.

The microcomputer 110 executes a sensor startup control process as shown in FIG. 7 upon receipt of a command signal from the ECU 200 at the restart of the internal combustion engine. Herein, steps S10, S12, S14, S16, S18 and S20 are common to the first and second embodiments.

At step S42, the microcomputer 110 initiates preliminary drive control of the Ip2 cell 30 after the processing of step S20.

At step S30, the microcomputer 110 connects the switching terminals SW7 and SW8 of the switching circuit 129 and causes the constant current circuit 128 to supply the constant electric current Ip3 to the Ip2 cell 30.

At step S31, the microcomputer 110 connects the switching terminals SW4 and SW6 of the switching circuit 309 and inputs the second input voltage to the input terminal 303 of the operational amplifier 301 so that the operational amplifier 301 of the Vp2 application circuit 127 sets the upper limit Vli on the voltage between the porous electrodes 32 and 33 of the Ip2 cell 30 during the preliminary drive control.

At step S31, the microcomputer 110 starts the timer 110a.

At step 34, the microcomputer 110 checks whether the timer 110a has timed out. When the timer 110a has timed out (Yes at step S34), the microcomputer 110 judges that the sensor element 1 has entered the stable/ready state and terminates the preliminary drive control of the Ip2 cell 30. The control then goes to step S44 to switch from the preliminary drive control to the normal drive control of the Ip2 cell 30. When the timer 110a has not timed out (No at step S34), the microcomputer 110 continues monitoring of the timer 110a.

At step S44, the microcomputer 110 connects the switching terminals SW4 and SW5 of the switching circuit 309 and inputs the first input voltage to the noninverting input terminal 303 of the operational amplifier 301 so that the operational amplifier 310 outputs the drive voltage Vp2 to the Ip2 cell 30 for NOx concentration measurement.

It is therefore possible in the second embodiment to ensure the substantially uniform, shortened stabilization time of the sensor element 1, regardless of the H$_2$O concentration in the gas under measurement, by performing the preliminary drive control of the Ip2 cell 30 after the startup of the sensor element 1 and before the normal drive control of the Ip2 cell 30 as in the first embodiment. It is also possible in the second embodiment to prevent breakage of the Ip2 cell 30 during the preliminary drive control by limiting the voltage between the porous electrodes 32 and 33 to be lower than such an upper limit value Vli that avoids blackening of the solid electrolyte layer 31 due to overvoltage between the porous electrodes 32 and 33. Furthermore, the microcomputer 110 (the processing of step 31) and the operational amplifier 301 constitute a voltage limit means to set the upper limit on the voltage between the porous electrodes 32 and 33 of the Ip2 cell 30 during the preliminary drive control; and the microcomputer 110 and (the processing of step 44) and the operational amplifier 301 constitute a voltage setting means to set the drive voltage Vp2 of the Ip2 cell 30 during the normal drive control in the second embodiment. The use of a single operational amplifier 301 as the voltage setting means and as the voltage limit means enables reduction in parts count for structural simplification of the sensor control apparatus 100.

The entire contents of Japanese Patent Application No. 2008-309504 (filed on Dec. 4, 2008) and No. 2009-238503 (filed on Oct. 15, 2009) are herein incorporated by reference.

Although the present invention has been described with reference to the above-specific embodiments of the invention, the invention is not limited to these exemplary embodiments. Various modification and variation of the embodiments described above will occur to those skilled in the art in light of the above teachings.

In the first and second embodiments, the temperature of the sensor element 1 is determined based on the internal resistance Rpvs of the Vs cell 20. Alternatively, the temperature of the sensor element 1 can be determined based on the internal resistance of the Ip1 cell 10, the internal resistance of the Ip2 cell 30 or the resistance of the heater element 61 (heater pattern 64).

Although the gas sensor (sensor element 1) is specifically designed for NOx concentration measurement in the first and second embodiments, the application of the preliminary cell drive control is not limited to the NOx sensor. The preliminary cell drive control can also be applied to any type of gas sensor, other than the NOx sensor, that utilizes the oxygen pumping cell with the oxygen ion conductor.

In the second embodiment, the Vp2 application circuit 127 is equipped with the operational amplifier 301 so as to perform the functions of applying the drive voltage Vp2 to the Ip2 cell 30 during the normal drive control and of setting the upper limit on the voltage between the porous electrodes 32 and 33 of the Ip2 cell 30 during the preliminary drive control. The circuit configuration of the Vp2 application circuit 127 is not however particularly limited to that of the second embodiment. Another operational amplifier (such as a known voltage regulator) may be provided separately from the operational amplifier 301 to regulate the voltage between the porous electrodes 32 and 33 of the Ip2 cell 30 to the limit level.

The scope of the invention is defined with reference to the following claims.

What is claimed is:

1. A control method for a gas sensor, the gas sensor comprising a sensor element equipped with first and second oxygen pumping cells to define first and second measurement chambers so that a gas under measurement first flows in the first measurement chamber and then flows from the first measurement chamber into the second measurement chamber, each of the first and second oxygen pumping cells having an oxygen ion conductor and a pair of electrodes arranged on the oxygen ion conductor, the control method comprising:

driving the first oxygen pumping cell in such a manner that the first oxygen pumping cell pumps oxygen in or out of the first measurement chamber to adjust the oxygen concentration of the gas in the first measurement chamber;

driving the second oxygen pumping cell with the application of a drive voltage between the electrodes of the second oxygen pumping cell in such a manner that the second oxygen pumping cell pumps oxygen out of the second measurement chamber to produce a flow of electric current between the electrodes of the second oxygen pumping cell in accordance with the amount of the oxygen pumped by the second oxygen pumping cell;

determining the concentration of a specific gas in the gas under measurement based on the electric current between the electrodes of the second oxygen pumping cell; and performing specific drive control by supplying a constant current to the second oxygen pumping cell for a predetermined time period in such a manner as to control the amount of the oxygen pumped by the second oxygen pumping cell to a predetermined level after startup of the sensor element and before the application of the drive voltage between the electrodes of the second oxygen pumping cell.

2. A control apparatus for a gas sensor, the gas sensor comprising a sensor element equipped with first and second oxygen pumping cells to define first and second measurement chambers so that a gas under measurement first flows in the first measurement chamber and then flows from the first measurement chamber into the second measurement chamber, each of the first and second oxygen pumping cells having an oxygen ion conductor and a pair of electrodes arranged on the oxygen ion conductor, the control apparatus being programmed to:

drive the first oxygen pumping cell in such a manner that the first oxygen pumping cell pumps oxygen in or out of the first measurement chamber to adjust the oxygen concentration of the gas in the first measurement chamber;

drive the second oxygen pumping cell with the application of a drive voltage between the electrodes of the second oxygen pumping cell in such a manner that the second oxygen pumping cell pumps oxygen out of the second measurement chamber to produce a flow of electric current between the electrodes of the second oxygen pumping cell in accordance with the amount of the oxygen pumped by the second oxygen pumping cell;

determine the concentration of a specific gas in the gas under measurement based on the electric current between the electrodes of the second oxygen pumping cell; and perform specific drive control by supplying a constant current to the second oxygen pumping cell for a predetermined time period in such a manner as to control the amount of the oxygen pumped by the second oxygen pumping cell to a predetermined level after startup of the sensor element and before the application of the drive voltage between the electrodes of the second oxygen pumping cell.

3. The control apparatus according to claim 2, wherein the control apparatus is configured to read any information correlated with a temperature of the sensor element and initiate said specific drive control when the temperature of the sensor element becomes higher than or equal to a reference temperature.

4. The control apparatus according to claim 2, wherein the control apparatus is configured to set an upper limit on the voltage between the electrodes of the second oxygen pumping cell during said specific drive control.

5. The control apparatus according to claim 4, further comprising an operational amplifier with a noninverting input terminal, an inverting input terminal and an output terminal, the inverting input terminal and the output terminal being electrically connected to each other, wherein the operational amplifier sets the drive voltage between the electrodes of the second oxygen pumping cell when a first input voltage is inputted to the noninverting input terminal and sets the upper limit on the voltage between the electrodes of the second oxygen pumping cell when a second input voltage higher than the first input voltage is inputted to the noninverting input terminal during said specific drive control.

* * * * *